US006344566B1

(12) United States Patent
Bathe et al.

(10) Patent No.: US 6,344,566 B1
(45) Date of Patent: Feb. 5, 2002

(54) METHOD FOR PRODUCING ENANTIOMER-FREE N-METHYL-N-[(1S)-1-PHENYL-2-((3S)-3-HYDROXYPYROLIDINE-1-YL)ETHYL]-2,2-DIPHENYLACETAMIDE

(75) Inventors: Andreas Bathe, Darmstadt; Bernd Helfert; Karl-August Ackermann, both of Ober-Ramstadt; Rudolf Gottschlich, Reinheim; Ingeborg Stein, Rodgau; Jens Budak, Darmstadt, all of (DE)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 09/647,813

(22) PCT Filed: Apr. 16, 1999

(86) PCT No.: PCT/EP99/02574

§ 371 Date: Jan. 26, 2001

§ 102(e) Date: Jan. 26, 2001

(87) PCT Pub. No.: WO99/02574

PCT Pub. Date: Oct. 5, 2000

(30) Foreign Application Priority Data

Apr. 20, 1998 (DE) .......................................... 198 17 393
Jun. 20, 1998 (DE) .......................................... 198 27 633

(51) Int. Cl.[7] .......................... C07D 207/04; A01N 1/00
(52) U.S. Cl. ........................ 548/541; 548/556; 548/550

(58) Field of Search ................................ 548/541, 556, 548/550; 514/424

(56) References Cited

U.S. PATENT DOCUMENTS 5,585,500 A * 12/1996 Drauz et al. ................. 548/541
6,060,504 A * 5/2000 Stein et al. .................. 514/428

OTHER PUBLICATIONS

Barber et al.: "A pharmaceutical profile of the novel peripherally–selective kappa–opiod receptor agonist, EMD 61753" vol. 113, No. 4 British Journal of Pharmacology (Dec. 1, 1994).
Gottschlich R et al.: "EMD 61753 as a favorable representative of structurally novel arylacetamido–type K opiate receptor agonists" Bioorganic & Medicinal Chemistry Letters, Bd. 4, Nr. 5, Jan. 1, 1994.

* cited by examiner

*Primary Examiner*—Floyd D. Higel
*Assistant Examiner*—Golam M. M. Shameem

(57) ABSTRACT

The invention relates to a novel process for the alternative preparation of N-methyl-N-[(1S)-1-phenyl-2-((3S)-3-hydroxypyrrolidin-1-yl)ethyl]-2,2-diphenylacetamide or N-methyl-N-[(1R)-1-phenyl-2-((3R)-3-hydroxypyrrolidin-1-yl)ethyl]-2,2-diphenylacetamide, and the novel compounds N-methyl-N-[(1S)-1-phenyl-2-((3S)-3-hydroxypyrrolidin-1-yl)ethane] and N-methyl-N[(1R)-1-phenyl-2-((3R)-3-hydroxypyrrolidin-1-yl) ethane], which are prepared as intermediates.

16 Claims, No Drawings

METHOD FOR PRODUCING ENANTIOMER-FREE N-METHYL-N-[(1S)-1-PHENYL-2-((3S)-3-HYDROXYPYROLIDINE-1-YL)ETHYL]-2,2-DIPHENYLACETAMIDE

This application is a 371 of PCT/EP99/02574 Apr. 16, 1999.

The invention relates to a novel process for the alternative preparation of N-methyl-N-[(1S)-1-phenyl-2-((3S)-3-hydroxypyrrolidin-1-yl)ethyl]-2,2-diphenylacetamide or N-methyl-N-[(1R)-1-phenyl-2-((3R)-3hydroxypyrrolidin-1-yl)ethyl]-2,2-diphenylacetamide, and the novel compounds N-methyl-N-[(1S)-1-phenyl-2-((3S)-3-hydroxypyrrolidin-1-yl)ethane] and N-methyl-N-[(1R)-1-phenyl-2-((3R)-3-hydroxypyrrolidin-1-yl) -ethane], which are formed as intermediates in this process.

As described by Barber et al. (B. J. Pharmacol. (1994), 113, 1317–1327), both the compound N-methyl-N-[(1S)-1-phenyl-2-((3S)-3-hydroxypyrrolidin-1-yl)ethyl]-2,2-diphenylacetamide and its physiologically tolerable salts have valuable pharmacological properties such as an analgesic, anti-inflammatory and aquaretic action, so that they are particularly suitable for the production of medicaments.

It has been found, as described in the Patent Application DE 1 95 23 502 or EP 752 246, that this compound is a particularly efficacious compound which is suitable as a medicament for the treatment of inflammatory intestinal disorders in a very particular manner. In particular, this compound is employable and efficacious in this indication, since it simultaneously alleviates the pain associated with this disorder and, in the acute case of an intestinal occlusion threatening or produced due to the inflammatory intestinal disorder, again normalizes or sets in motion the motor response of the intestine without producing noticeable side effects. Moreover, the compound can be employed in non-inflammatory intestinal disorders such as IBS (irritable bowel syndrome).

The Patent Applications DE 40 34 785 A1 and DE 42 15 213 A1 or EP 0 569 802 A1 describe the preparation of N-methyl-N-[(1S)-1-phenyl-2-((3S)-3-hydroxypyrrolidin-1-yl) ethyl]-2,2-diphenylacetamide by reaction of (2S)-2-N-carboxyethyl-2-phenylglycin-N,N-[(3S)-3-hydroxytetramethylamide with diphenylacetyl chloride. As described in DE 42 15 213, the starting compound (2S)-2-N-carboxyethyl-2-phenylglycin-N,N-[(3S)-3-hydroxytetramethyleneamide, also known as (1S)-[1-N-methylamino-1-phenyl-2-((3S)-3-hydroxypyrrol idino) ethane can be prepared by reacting (1S)-1-amino-1-phenyl-2-chloroethane with (3S)-3-hydroxypyrrolidine and then methylating with methyl iodide. The problems of this preparation method, however, are the solubility of the starting products and that following the synthesis the racemic product mixture obtained, which is contaminated by by-products, has to be laboriously separated. The process known until now for the preparation of N-methyl-N-[(1S)-1-phenyl-2-((3S)-3-hydroxypyrrolidin-1-yl)ethyl]-2,2-diphenylacetamide is therefore laborious and expensive and results in low yields based on the starting compounds employed.

It was therefore the object of the present invention to make available a process, which can be carried out in a simple manner and economically, for the preparation of N-methyl-N-[(1S)-1-phenyl-2-((3S)-3hydroxypyrrolidin-1-yl)ethyl]-2,2-diphenylacetamide or, when using the enantiomeric starting materials, of N-methyl-N-[(1R)-1-phenyl-2-((3R)-3-hydroxypyrrolidin-1-yl)ethyl]-2,2-diphenylacetamide, which starts from economical, readily soluble starting materials which result in a product which is as enantiomerically pure as possible, which can then be isolated and purified in a simple manner.

The object is achieved by a process according to claim 1, either the previously unknown compound N-methyl -N-[(1S)-1-phenyl-2-((3S)-3-hydroxypyrrolidin-1-yl)ethane]-yl)etane] being used as a novel intermediate for the preparation of N-methyl-N-[(1S)-1-phenyl-2-((3S)-3-hydroxypyrrolidin-1-yl)ethyl]-2,2-diphenylacetamide or N-methyl-N-[(1R)-1-phenyl-2-((3R)-3-hydroxypyrrolidin1-yl)ethane] being used as a novel intermediate for the preparation of N-methyl-N-[(1R)-1-phenyl-2-((3R)-3hydroxypyrrolidin-1-yl)ethyl]-2,2-diphenylacetamide.

It has been found that compounds of the formula (III)

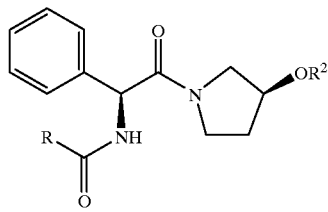

(III)

in which R and $R^2$ have the following meanings,

R is H, $OR^1$ or $SR^1$, $R^1$ is A, aryl, heteroaryl, $Si(R^3)_3$ or $COR^3$, $R^2$ is H, A, aryl, heteroaryl and $Si(R^3)_3$ or $COR^3$, $R^3$ is H, A, aryl or heteroaryl, A is a straight-chain or branched alkyl radical having 1 to 6 C atoms, can be prepared in high yields and in enantiomerically pure form by amidically coupling, depending on the final product desired, (3S)-3-hydroxypyrrolidines or (3R)-3-hydroxypyrrolidines of the formula (II)

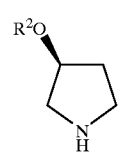

(II)

in which $R^2$ is H, A, aryl, heteroaryl and $Si(R^3)_3$ or $COR^3$ and $R^3$ is H, A, aryl or heteroaryl or their salts, formed with HCl, HBr, HI, $H_2SO_4$, $H_3PO_4$ or suitable organic acids, with appropriate (S)- or (R)-enantiomeric forms of N-substituted phenylglycines of the formula (I)

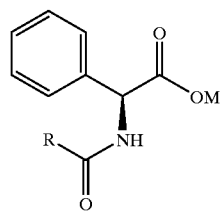

(I)

in which

R is H, $OR^1$ or $SR^1$, $R^1$ is A, aryl, heteroaryl, $Si(R^3)_3$ or $COR^3$, $R^3$ is H, A, aryl or heteroaryl, M is H or a cation from the group consisting of alkali metal, alkaline earth metal, ammonium or alkylammonium.

Alkyl has 1 to 6, preferably 1, 2, 3 or 4, C atoms. Alkyl is preferably methyl, furthermore ethyl, propyl, isopropyl, butyl, isobutyl, sec-butyl or tert-butyl, furthermore also pentyl, 1-, 2- or 3-methylbutyl, 1,1-, 1,2-or 2,2-dimethylpropyl, 1-ethylpropyl, hexyl, 1-, 2-, 3- or 4-methylpentyl, 1,1-, 1,2-, 1,3-, 2,2-, 2,3-or 3,3-dimethylbutyl, 1-or 2-ethylbutyl, 1-ethyl-1-methylpropyl, 1-ethyl-2-methylpropyl, 1,1,2-or 1,2,2-trimethylpropyl.

Aryl is preferably unsubstituted phenyl or phenyl which is mono- or disubstituted by Hal, OA or alkyl, furthermore, for example, biphenyl or naphthyl.

Heteroaryl is preferably, for example, furanyl, thiophenyl, pyridinyl, pyrrolyl or thiazolyl.

$Si(R^3)_3$ is preferably, for example, $Si(CH_3)_3$.

$COR^3$ is preferably, for example, acetyl or benzoyl.

R is preferably, in particular, for example, methoxy or ethoxy.

$R^1$ is in particular, for example, methyl, ethyl, propyl, butyl, phenyl, $Si(CH_3)_3$ or acetyl.

$R^2$ is, in particular, for example, H, tert-butyl, $Si(CH_3)_3$, acetyl, benzyl or benzoyl, very particularly preferably it is H.

The amides of the formula (III) prepared can be converted in a simple manner reductively, if appropriate by removal of the protective group from the hydroxyl group of the pyrrolidine in N-methyl-N-[(1S)-1-phenyl-2-((3S)-3-hydroxypyrrolidin-1-yl) ethane] or N-methyl -N-[(1R)-1-phenyl-2-((3R)3-hydroxypyrrolidin-1yl)ethane] of the formula (IV).

By reaction with activated carboxylic acids of the formula (V)

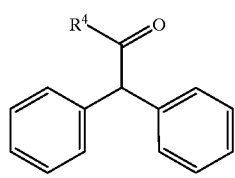

(V)

in which $R^4$ is F, Cl, Br, I, OA or O—CO—A, it is possible to obtain from the free bases of the compounds of the formula (IV)

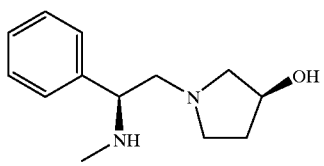

(IV)

or from their salts, formed with HCl, HBr, HI, $H_2SO_4$, $H_3PO_4$ or suitable organic acids, the enantiomeric compounds of the formula (VI)

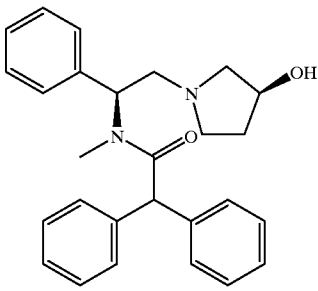

(VI)

in pure form. Preferably, these compounds are prepared as hydrochlorides, the compound N-methyl-N-[(1S)-1-phenyl-2 -((3S)-3-hydroxypyrrolidin-1-yl)ethyl]-2,2-diphenylacetamide being the known form EMD 61753; but the corresponding salts with the other abovementioned acids can also be prepared analogously.

In particular, N-methyl-N-[(1S)-1-phenyl-2((3S)-3-hydroxypyrrolidin-1-yl)ethyl]-2,2-diphenylace-amide can be prepared by the last reaction with diphenylacetyl chloride.

The compounds of the formula (IV) synthesized as intermediates can generally be obtained by reaction of compounds of the formula (I) with those of the formula (II). Preferably, compounds of the formula (I) are used in this reaction in which R has the meaning $OR^1$ where $R^1$ is A, aryl, heteroaryl, $Si(R^3)_3$ or $COR^2$ and $R^2$ is H, alkyl, aryl or heteroalkyl, having the preferred meanings indicated above. Surprisingly, in contrast to the use of the corresponding formyl compound, enantiomerically pure reaction products of the formula (III) are obtained. In this manner, the resolution of the racemate can advantageously be omitted.

The reaction of the compounds (I) and (II) can be carried out in any desired aprotic solvent. Particularly suitable solvents are polar aprotic solvents from the group consisting of diethylether, petroleum ether, acetone, nitrobenzene, dimethyl-formamide, dimethyl sulphoxide or other corresponding solvents. In this connection, the starting materials are taken up in sufficient solvent such that a 10 to 30 percent solution is obtained. Preferably, the reaction is carried out in tetrahydrofuran as a solvent.

The reactions of the compounds (I) and (II) are carried out under suitable conditions at temperatures between 0 and 50° C. Particularly good results, however, are achieved at room temperatures between 20 and 30° C. and at normal pressure.

For the activation of the starting materials, the presence of an auxiliary reagent is necessary. These can be auxiliaries which are also used as peptide coupling reagents. Suitable compounds are those such as, for example, phosphorus oxytrichloride, phosphorus halides of valency III and V, phosgene, dicyclohexylcarbodiimide, the tributylammonium salt of pyridine, phenyl dichlorophosphate, 2-chloro-1,2,3-trinitrobenzene, phosphoric acid esters, chlorosulphonyl isocyanate, $CH_3SO_2Cl$-$(C_2H_5)_3N$, $(C_6H_5)_3P$-$CCl4$-$(C_2H_5)_3N$, N,N'-carbonyldiimidazole, N-(alkylcarbonyl) -imidazoles, acid anhydrides or acid chlorides and in particular alkyl chloroformates, such as ethyl chloroformate. Other suitable auxiliary reagents are described in various reference books, such as, for example, in C. Ferri "Reaktionen der organischen Synthese" ["Reactions of Organic Synthesis"]; R. C. Larock "Comprehensive Organic Transformations; A Guide to Functional Group Preparations", Verlag Chemie, 1989.

Furthermore, the presence of a base is necessary. Suitable bases can likewise be inferred from the abovementioned reference books. Such bases are, for example, tertiary amines, such as, for example, triethylamine. However, inorganic bases can also be added. Suitable inorganic bases are, in particular, carbonates. When using the alkyl metal hydroxides, such as NaOH or KOH, attention is particularly to be paid to exact addition, since otherwise undesired side reactions occur. For simplification of the work-up, however, it is also possible to employ the hydroxypyrrolidine in an excess, so that it acts as a base itself.

The work-up of the reaction product (III) obtained can be carried out from the filtrate after filtering off the precipitate obtained using customary laboratory methods. For example, a customary and suitable method consists in distilling off the solvent, taking up the crude product again in an organic solvent, extracting the solution obtained with water a umber of times, distilling off the solvent again and recrystallizing the product obtained by recrystallization from a suitable solvent, such as, for example, from methanol. However, other working-up variants known to the person skilled in the art are also possible, such as, for example, those which additionally include a chromatographic purification.

Depending on the reaction conditions, the reaction product (III) is obtained from a water-containing solvent mixture as a free base or as an acid addition salt of the acids HCl, HBr, HI, $H_2SO_4$ or of an organic carboxylic acid. In the latter cases, the isolation can be carried out after the phase separation according to customary laboratory methods.

Suitable organic carboxylic acids which can be used are, in particular, aliphatic, alicyclic, araliphatic, aromatic or heterocyclic mono- or polybasic carboxylic, sulphonic or sulphuric acids, e.g. formic acid, acetic acid, propionic acid, pivalic acid, diethylacetic acid, malonic acid, succinnic acid, pimelic acid, fumaric acid, maleic acid, lactic acid, tartaric acid, malic acid, citric acid, gluconic acid, ascorbic acid, nicotinic acid, isonicotinic acid, methane- or ethanesulphonic acid, ethanedisulphonic acid, 2-hydroxyethanesulphonic acid, benzenesulphonic acid, p-toluenesulphonic acid, naphthalene-mono- and -disulphonic acids, lauryl sulphuric acid.

The compounds of the formula (III) are reduced under a protective gas atmosphere, e.g. under a nitrogen atmosphere, in the presence of a hydride transfer reagent. Suitable hydride transfer reagents are those from the group consisting of the metal aluminium hydrides, preferably lithium aluminium hydride, metal alkoxyaluminium hydrides, such as, for example, Li triethoxyaluminium hydride, metal borohydrides, preferably $NaBH_4$, or borane, the presence of a Lewis acid additionally being necessary, such as, for example, boron trifluoride.

The reduction is preferably carried out in a polar aprotic and hydride-inert solvent. Suitable solvents are the same as already mentioned above. Particularly suitable solvents are, for example, diethylether or tetrahydrofuran.

To carry out the hydrogenation, a compound of the formula (III) is dissolved in a suitable solvent and added with warming to a solution which contains the hydride transfer reagent in equimolar amounts or in a small excess. However, it is also possible to introduce the starting compound to be hydrogenated and to add the hydrogenation reagent in an appropriate amount in a suitable manner such that a reaction mixture is obtained in which the starting material has a concentration of 10 to 25% by, weight, based on the solvent. To complete the reaction, the reaction mixture is stirred under reflux conditions for a number of hours. The reaction solution is then processed according to methods known to the person skilled in the art, by decomposing, inter alia, by addition of a solvent mixture consisting of a proton-yielding and an aprotic solvent, the excess of hydride transfer reagent and liberating the reaction product. Suitable proton-yielding solvents are, for example, water or alcohols such as ethanol or methanol. Suitable aprotic solvents are all polar aprotic solvents already mentioned above, in particular tetrahydrofuran. The latter is preferably employed, since it is obtainable industrially as an anhydrous product.

Product work-up can be carried out after phase separation according to customary laboratory methods. The crude product obtained can be worked up by crystallization methods or, for work-up, it is taken up, for example, in an organic water-immiscible solvent and treated with an excess of an inorganic acid, preferably hydrochloric acid. The salt formed in this manner can then be separated off in crystalline form.

The further reaction of N-methyl-N-[(1S)-1-phenyl-2-((3S)-3-hydroxypyrrolidin-1-yl)ethane or its dihydrochloride with a suitable diphenyl acetic acid derivative, preferably the acid chloride, to give the desired final product N-methyl-N-[(1S)-1-phenyl-2 -((3S)-3-hydroxypyrrolidin-1-yl)ethyl]-2,2-diphenylacet-amide (formula VI, EMD 61753) is carried out according to methods such as are described in DE-A1-40 34 785 and DE-A1-42 15 213 or EP 0 569 802 A1.

The examples given below are given for illustration of the present invention, but cannot be used to restrict the claimed invention thereto, since different variations of the examples are possible and lead to the desired product N-methyl-N-[(1S)-1-phenyl-2-((3S)-3-hydroxypyrrolidin-1-yl)ethane [formula (IV)], which can be used as an intermediate for the preparation of N-methyl-N-[(1S)-1-phenyl-2-((3S)-3-hydroxypyrrolidin-1-yl)ethyl]-2,2-diphenylacetamide.

EXAMPLES

N-Substituted (2S)-2-phenylglycine-N,N-[(3S)-3-hydroxytetramethyleneamides] of the formula III from (2S)-phenylglycines of the formula I

Example 1

(2S)-N-Formyl-2-phenylglycine-N,N-[(3S)-3-hydroxytetra-methyleneamide

From (2S)-N-formyl-2-phenylglycine (obtainable from (S)-(+)-alpha-aminophenylacetic acid and acetic anhydride/formic acid, e.g. according to Huszthy, Peter; Oue, Masatoshi; Bradshaw, Jerald S.; Zhu, Cheng Y.; Wang, Tingmin; et al., J. Org. Chem., EN, 57 (20) [1992] 5383–5394) and (3S)-3-hydroxypyrrolidine (obtainable from commercial (S)-1-benzyl-3-pyrrolidinole, e.g. according to Bhat, Krishna L.; Flanagan, Denise M.; Joullie, Madeleine M., Synth. Commun., EN, 15 (7) [1985] 587–598 or Naylor, Alan; Judd, Duncan B.; Scopes, David I. C.; Hayes, Ann G.; Birch, Philip J., J. Med. Chem., EN, 37 (14) [1994] 2138–2144):

Under a nitrogen atmosphere, 4.8 ml of ethyl chloroformate in 10 ml of tetrahydrofuran are added with stirring to 9 g of (2S)-N-formyl-2-phenylglycine and 5.5 ml of N-methylmorpholine in 250 ml of THF at −15° C. and, after a waiting time of 10 min, a solution of 6.2 g of (3S)-3-hydroxypyrrolidine hydrochloride and 7 ml of triethylamine in 50 ml of dimethylformamide. After stirring for 18 hours, the precipitate obtained is separated off and resultant (2S)-N-formyl-2-phenylglycine-N,N-[(3S)-3-hydroxytetramethyleneamide is isolated from the filtrate by concentration using customary laboratory methods, and a subsequent chromatographic purification.

1H-NMR: $D_6$-DMSO; 3.0–3.8 (m), 4.25 (d), 5.0 (s,br), 5.7 (dd), 7.4 (ArH), 8.0 (ArH), 8.8 (CHO):

MS-FAB: $(M+1)^+$ 221, 205;

Crystals m.p.: 97–101° C.;

$[\alpha]D^{20}=+208°$; C=1 in methanol.

Example 2

(2S)-N-Carboxybenzyl-2-phenylglycine-N,N-[(3S)-3-hydroxytetramethyleneamide

From (2S)-N-carboxybenzyl-2-phenylglycine (from (S)-(+)-alpha-aminophenylacetic acid and benzyl chlorocarbonatel for example, according to Jones, Raymond C F; Turner, Ian; Howard, Kevin J., Tetrahedron Lett., 34 (39) [1993] 6329–6332) and (3S)-3-hydroxypyrrolidine (obtainable from commercial (S)-1-benzyl-3-pyrrolidinole, for example, according to Bhat, Krishna L.; Flanagan, Denise M.; Joullie, Madeleine M., Synth. Commun., EN, 15 (7) [1985] 587–598 or Naylor, Alan; Judd, Duncan B.; Scopes, David I. C.; Hayes, Ann G.; Birch, Philip J., J. Med. Chem., EN, 37 (14) [1994] 2138–2144):

Under a nitrogen atmosphere, 14.3 g of (2S)-N-carboxybenzyl-2-phenylglycine in 100 ml of tetrahydrofuran are treated in the cold with 5.5 ml of 4-methyl-morpholine and a solution of 4.8 ml of ethyl chloroformate and 10 ml of tetrahydrofuran and then stirred for 30 min. A solution of 4.36 g of (3S)-3-hydroxypyrrolidine and 10 ml of tetrahydrofuran is then added. After stirring for 18 hours, the precipitate obtained is separated off and the (2S)-N-carboxybenzyl-2-phenylglycine-N,N-[(3S)-3-hydroxytetramethyleneamide formed is isolated from the filtrate by concentrating using customary laboratory methods, taking up in an organic solvent, washing with an aqueous phase, concentrating again and crystallization.

1H-NMR: $D_6$-DMSO+TFA; 5.1 (s), PhCH$_2$R;

FAB-MS: 355 $(M+1)^+$, 311, 196, 176; Consistency: Oil;

$[\alpha]D^{20}=+108°$; C=1 in methanol.

Example 3

(2S)-N-Carboxyethyl-2-phenylglycine-N,N-[(3S)-3-hydroxytetramethyleneamide 3.a)

From (2S)-N-carboxyethyl-2-phenylglycine (from (S)-(+)-alpha-aminophenylacetic acid and ethyl chlorocarbonate, for example, according to Bodurow, C. C.; Boyer, B. D.; Brennan, J.; Bunnell, C. A.; Burks, J. E.; et al., Tetrahedron Lett., EN, 30 (18) [1989] 2321–2324) and (3S)-3-hydroxypyrrolidine (obtainable from commercial (S)-1-benzyl-3-pyrrolidinole, for example, according to Bhat, Krishna L.; Flanagan, Denise M.; Joullie, Madeleine M., Synth. Commun., EN, 15 (7) [1985] 587–598 or Naylor, Alan; Judd, Duncan B.; Scopes, David I. C.; Hayes, Ann G.; Birch, Philip J., J. Med. Chem., EN, 37 (14) [1994] 2138–2144):

under a nitrogen atmosphere, 16.7 g of (2S)-N-carboxyethyl-2-phenylglycine are treated in the cold with 8.3 ml of 4-methylmorpholine and a solution of 7.1 ml of ethyl chloroformate and 20 ml of tetrahydrofuran and then stirred for 60 min A solution of 6.5 g of (3S)-3-hydroxypyrrolidine and 30 ml of tetrahydrofuran is then added. After stirring for 18 hours, the precipitate obtained is separated off and resultant (2S)-N-carboxyethyl-2-phenylglycine-N,N[-(3S)-3-hydroxytetramethyleneamide is isolated from the filtrate by concentrating using customary laboratory methods, taking up in an organic solvent, washing with an aqueous phase, concentrating again and crystallization.

3.b)

From (2S)-N-carboxyethyl-2-phenylglycine (see above) and (3S)-3-hydroxypyrrolidine hydrochloride (commercially obtainable): a mixture of 24 g of (2S)-N-carboxyethyl-2-phenylglycine with 10 g of methylmorpholine in 100 ml of THF is added at about −10° C. to 11 g of ethyl chloroformate in 100 ml of THF. After a stirring phase, this is followed by a mixture of 12 g of (3S)-3-hydroxypyrrolidine hydrochloride in 10 ml of deionized water and a mixture of 10 g of methylmorpholine in 20 ml of THF. After stirring for a number of hours and phase separation, the (2S)-N-carboxyethyl-2-phenylglycine-N,N-[(3S)-3-hydroxytetra-methyleneamide is isolated using customary laboratory methods by concentrating, taking up in an organic solvent, washing with an aqueous phase, concentrating it again and crystallization.

The analytical data for the variants 3a and 3b correspond:

1H-NMR: $D_6$-DMSO; 1.2 (t), 3–3.8 (m, br), 4.05 (q), 4.25 (s,br), 7.25–7.45 (m);

MS: 293 $(M+1)^+$, 247, 178, 106;

Crystals m.p.: 124–126° C.;

$[\alpha]D^{20}=+137°$ C. 1 in methanol.

N-Methyl-N-[(1S)-1-phenyl-2-((3S)-3-hydroxypyrrolidin1-yl)ethane of the formula IV

Example 4

N-Methyl-N-[(1S)-1-phenyl-2-((3S)-3-hydroxypyrrolidin-1-yl)ethane=1-[(3S)-3-Hydroxypyrrolidin-1-yl]-(2S)-2-methylamino-2-phenylethane Under nitrogen, 2200 ml of a 1.08 molar lithium aluminium hydride-tetrahydrofuran solution are gently warmed and a solution of 264 g of (2S)-N-carboxyethyl2-phenylglycine-N,N-[(3S)-3-hydroxytetramethyleneamide] and 1400 ml of tetrahydrofuran are added with stirring. After the end of the addition, the mixture is refluxed for 3 hours and the cooled reaction solution is hydrolyzed by means of a water/tetrahydrofuran mixture. After sodium carbonate treatment and removal of inorganic constituents, the product is isolated from the filtrate using customary laboratory methods. The oily crude product forms a solid after purification by means of crystallization or chromatography.

1H-NMR: $D_6$-DMSO; 2.1–3.1 (m), 3.6 (dd), 4.3 (m), 7.15–7.35 (m);

MS: 220 $(M^+)$, 205, 120, 100, 91; Appearance: Yellowish oil which crystallizes depending on the batch;

$[\alpha]D^{20}=+66.8°$; C=0.0938 g in 10 ml of methanol.

Example 5

N-Methyl-N-[(1S)-1-phenyl-2-((3S)-3-hydroxypyrrolidin-1-yl)ethane dihydrochloride=1-[(3S)-3-Hydroxypyrrolidin-1-yl]-(2S)-2-methylamino-2-phenylethane dihydrochloride Under nitrogen, 2200 ml of a 1.08 molar lithium aluminium hydride-tetrahydrofuran solution are gently warmed and a solution of 264 g of (2S)-N-carboxyethyl2-phenylglycine-N,N-[(3S)-3-hydroxytetramethyleneamide] and 1400 ml of tetrahydrofuran are added with stirring. After the end of the addition, the mixture is refluxed for a further 3 hours, then cooled and the reaction solution is hydrolyzed by means of a mixture of 80 ml of water and 400 ml of tetrahydrofuran. After sodium carbonate treatment and removal of inorganic constituents, the product is isolated from the filtrate using customary laboratory methods. The oily crude product is taken up in an organic, water-immiscible solvent and treated with an excess of hydrochloric acid. The crystalline product is isolated and dried.

1H-NMR: $D_6$-DMSO; 3.4 (m), 3.8 (m), 4.2 (m), 4.4 (m), 4.9 (m), 7.5 and 7.8 (ArH);

Melting point: 240–242° C.;

$[]D^{20}=-22.4°$; C=1 in water.

What is claimed is:
1. A process for the preparation of N-methyl-N-[(1S)-1-phenyl-2-((3S)-3-hydroxypyrrolidin-1-yl)ethyl]-2,2-diphenylacetamide or N-methyl-N-[(1R)-1-phenyl-2-((3R)-3-hydroxypyrrolidin-1-yl)]-2,2-diphenylacetamide comprising:

a) reacting an (S)- or (R)-enantiomeric form of

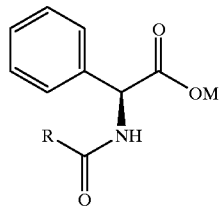

(I)

in which

R is $OR^1$ or $SR^1$, $R^1$ is A, aryl, heteroaryl, Si $(R^3)_3$ or $COR^3$, $R^3$ is H, A, aryl or heteroaryl, A is straight-chain or branched alkyl having 1 to 6 C atoms, M is H or an alkali metal, alkaline earth metal, ammonium or alkylammonium cation, with a (3S)-3-hydroxypyrrolidine or (3R)-3-hydroxypyrrolidine of the formula II

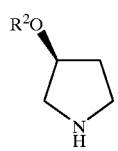

(II)

in which $R^2$ is H, A, aryl, heteroaryl, Si $(R^3)_3$ or $COR^3$ and $R^3$ is H, A, aryl or heteroaryl or with an acid addition salt of the compound of the formula (II), with an acid HCl, HBr, HI, $H_2SO_4$, $H_3PO_4$ or an organic carboxylic acid, to give a compound of the formula III

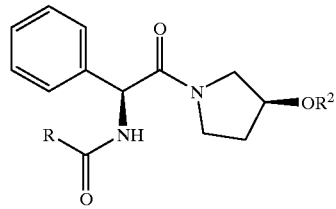

(III)

in which R and $R^2$ having the meanings given above, b) converting the compound of the formula III by reducing it to a compound of the formula (IV)

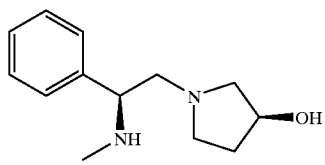

(IV)

and optionally converting the latter into a corresponding acid addition salt with an acid HCl, HBr, HI, $H_2SO_4$, $H_3PO_4$ or an organic carboxylic acid, and c) reacting the compound of the formula (IV) thus obtained with an activated carboxylic acid of the formula (V)

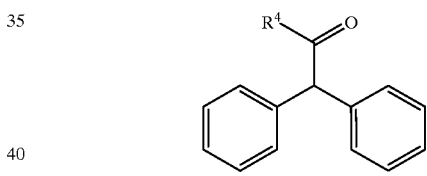

(V)

in which $R^4$ is F, Cl, Br, I, OA or O—CO—A, to give the compound of the formula (VI)

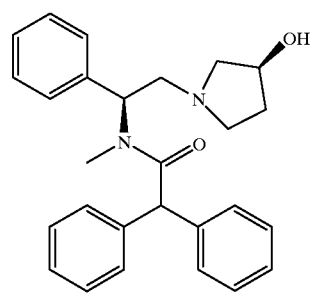

(VI)

and optionally converting the latter into the associated acid addition salt with HCl, HBr, HI, sulphuric acid, sulphamic acid, nitric acid, phosphoric acid, orthophosphoric acid, or an organic acid,
wherein the starting materials employed in stage a) are selected depending on the enantiomer desired as the final product.

2. N-methyl-N-[(1S)-1-phenyl-2((3)-3-hydroxypyrrolidin-1-yl)ethyl]-2,2-diphenylacetamide, or N-methyl-N-[(1R)-1-phenyl-2-((3R)-3hydroxypyrrolidin-1yl)ethyl]-2,2-diphenylacetamide.

3. A process according to claim 1, wherein R of the compounds of the formula (I) is $OR^1$ where $R^1$ is A, aryl, heteroaryl, Si $(R^3)_3$ or $COR^3$ wherein $R^3$ is H, A, aryl or heteroalkyl.

4. A process according to claim 1, wherein the reaction of the compounds (I) and (II) is carried out in an aprotic or polar aprotic solvent at a temperature from 0 to 50° C.

5. A process according to claim 1, wherein compounds of formulas (I) and (II) are present in a combined concentration of 10 to 30% in a solvent wherein the reaction of the compounds of formulas (I) and (II) is carried out in said solvent.

6. A process according to claim 1, wherein the reaction of the compounds (I) and (II) is carried out in the presence of an auxiliary reagent.

7. A process according to claim 1, wherein the reaction of the compounds (I) and (II) is carried out in the presence of a base.

8. A process according to claim 1, wherein the reduction of the compounds of the formula (III) is carried out in the presence of a hydride transfer reagent.

9. A process according to claim 1, wherein a compound of the formula (III) as a starting material is dissolved in a solvent in a concentration of 10 to 25% and the hydrogenation product is liberated by addition of a proton-yielding solvent in a mixture with an aprotic solvent.

10. A method for treating non-inflammatory intestinal disorders comprising administering the compound (N-methyl-N-[(1S)-1-phenyl-2-((3S)-3-hydroxypyrrolidin-1-yl)ethyl]-2,2-diphenylacetamide to a patient.

11. A process according to claim 4, wherein the temperature is between 20 and 30° C.

12. A process according to claim 5, wherein the solvent is diethyl ether, petroleum ether, acetone, nitrobenzene, dimethyl formamide, dimethyl sulphoxide, or tetrahydrofuran.

13. A process according to claim 6, wherein the auxiliary reagent is phosphorus oxytrichloride, a phosphorus halide of valency III and V, phosgene, dicyclohexylcarbodiimide, the tributylammonium salt of pyridine, phenyl dichlorophosphate, 2-chloro-1,2,3-trinitrobenzene, a phosphoric acid ester, chlorosulphonyl isocyanate, $CH_3SO_2Cl$—$(C_2H_5)_3N$, $(C_6H_5)_3P$—$CCl_4$—$(C_2H_5)_3N$,N,N'-carbonyldiimidazole, an N-(alkylcarbonyl) imidazole, acetic acid, acetyl chloride, ethyl chloroformate or an organic or inorganic base.

14. A process according to claim 7, wherein the base is triethylamine, sodium carbonate, potassium carbonate, calcium carbonate, NaOH, or KOH.

15. A process according to claim 8, wherein a hydride transfer reagent is a metal aluminum hydride, a metal alhoxyaluminum hydride, a metal borohydride, borane, or in the presence of a Lewis acid, a polar aprotic solvent.

16. A process according to claim 15, wherein independently of each other the metal aluminum hydride, the metal alhoxyaluminum hydride is Li triethoxyaluminum hydride, the metal borohydride is Na BH, the Lewis acid is boron trifluoride, and the polar aprotic solvent is diethyl ether, petroleum ether, acetone, nitrobenzene, dimethyl formamide, dimethyl sulfoxide or tetrahydrofuran.

* * * * *

UNITED STATES PATENT AND TRADEMARK OFFICE
CERTIFICATE OF CORRECTION

PATENT NO.    : 6,344,566 B1
DATED         : February 5, 2002
INVENTOR(S)   : Bathe et al.

It is certified that error appears in the above-identified patent and that said Letters Patent is hereby corrected as shown below:

Title page, Item [54] and Column 1, line 3,
Please correct a misspelled word in the title. Delete "HYDROXYPYROLIDINE" and insert -- HYDROXYPYRROLIDINE --.

Column 11,
Line 1, delete "((3)" and insert -- ((3S) --;
Line 3, delete "-3hydroxypyrrolinidin" and insert -- -3-hydroxypyrrolindin --.

Signed and Sealed this

Thirty-first Day of December, 2002

JAMES E. ROGAN
*Director of the United States Patent and Trademark Office*

UNITED STATES PATENT AND TRADEMARK OFFICE
Certificate

Patent No. 6,344,566 B1                                        Patented: February 5, 2002

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Andreas Bathe, Darmstadt, (DE); Bernd Helfert, Ober-Ramstadt, (DE); Karl-August Ackermann, Ober-Ramstadt, (DE); Rudolf Gottschlich, Reinheim, (DE); Ingeborg Stein, Rodgau, (DE); Jens Budak, Darmstadt, (DE); and Andrew Barber, Weiterstadt, (DE).

Signed and Sealed this Twenty-ninth Day of May 2007.

WILLIAM R. DIXON, JR.
*Special Program Examiner*
Technology Center 1600